US007806589B2

(12) United States Patent
Tashman et al.

(10) Patent No.: US 7,806,589 B2
(45) Date of Patent: Oct. 5, 2010

(54) BI-PLANE X-RAY IMAGING SYSTEM

(75) Inventors: Scott Tashman, Pittsburgh, PA (US);
Jim Princehorn, Sanford, FL (US);
Samson Pennatto, Sanford, FL (US);
William Anderst, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 12/236,733

(22) Filed: Sep. 24, 2008

(65) Prior Publication Data
US 2009/0080598 A1 Mar. 26, 2009

Related U.S. Application Data

(60) Provisional application No. 60/975,417, filed on Sep. 26, 2007.

(51) Int. Cl.
H05G 1/02 (2006.01)
H05G 1/00 (2006.01)
G01N 23/00 (2006.01)
(52) U.S. Cl. .............................. 378/197; 378/9; 378/193
(58) Field of Classification Search .................. 378/9, 378/92, 193, 195–197, 210
See application file for complete search history.

(56) References Cited

U.S. PATENT DOCUMENTS

| | | | | |
|---|---|---|---|---|
| 3,549,885 A | * | 12/1970 | Andersson | 378/189 |
| 4,104,527 A | * | 8/1978 | Tomita et al. | 378/11 |
| 4,127,775 A | * | 11/1978 | Ohlson | 378/91 |
| 4,187,429 A | * | 2/1980 | Tomita et al. | 378/17 |
| 4,287,424 A | * | 9/1981 | Tomita et al. | 378/11 |
| 4,759,048 A | * | 7/1988 | Ohlson | 378/197 |
| 4,964,152 A | * | 10/1990 | Kaul et al. | 378/198 |
| 5,073,917 A | * | 12/1991 | Van Endschot et al. | 378/197 |
| 5,148,467 A | * | 9/1992 | Sato et al. | 378/197 |
| 5,367,554 A | * | 11/1994 | Kobayashi et al. | 378/196 |
| 5,425,069 A | * | 6/1995 | Pellegrino et al. | 378/198 |
| 5,499,284 A | * | 3/1996 | Pellegrino et al. | 378/198 |
| 5,515,416 A | * | 5/1996 | Siczek et al. | 378/197 |

(Continued)

OTHER PUBLICATIONS

Anderst, W., Tashman, S. A method to estimate in vivo dynamic articular surface interaction. Journal of Biomechanics. 36 (2003). 1291-1299.

(Continued)

*Primary Examiner*—Edward J Glick
*Assistant Examiner*—Anastasia Midkiff
(74) *Attorney, Agent, or Firm*—Kegler Brown Hill & Ritter; James J. Pingor

(57) ABSTRACT

A high-speed biplane radiography system for in-vivo assessment of joint function is provided. The system can acquire stereo-pair radiographic images at rates from 30-4000 frames per second of nearly any motion or joint. The radiographic equipment can be mounted in a gantry system that provides sufficient positioning flexibility for imaging different joints of a subject's body, along with an imaging area large enough for a variety of dynamic activities (e.g., walking, running, jumping, throwing, etc.). Three-dimensional (3D) bone positions can be determined using software for matching the bones in each X-ray image with 3D models developed from subject-specific CT (computed tomography) scans. This system can provide accurate (e.g., ±0.1 mm) assessment and direct 3D visualization of dynamic joint function, and can overcome limitations of conventional gate or motion analysis.

20 Claims, 10 Drawing Sheets

U.S. PATENT DOCUMENTS

| | | | | |
|---|---|---|---|---|
| 5,923,721 A * | 7/1999 | Duschka | | 378/92 |
| 6,097,788 A * | 8/2000 | Berenstein et al. | | 378/92 |
| 6,104,780 A * | 8/2000 | Hanover et al. | | 378/92 |
| 6,872,000 B2 * | 3/2005 | Atzinger | | 378/197 |
| 6,909,769 B2 | 6/2005 | Bruder et al. | | |
| 7,016,454 B2 * | 3/2006 | Warnberg | | 378/9 |
| 7,018,097 B2 * | 3/2006 | Schmitt | | 378/197 |
| 7,020,235 B2 * | 3/2006 | Hornegger et al. | | 378/9 |
| 7,050,844 B2 * | 5/2006 | Strobel | | 600/424 |
| 7,448,800 B2 * | 11/2008 | Steger et al. | | 378/193 |
| 2003/0113006 A1 * | 6/2003 | Berestov | | 382/131 |
| 2004/0052334 A1 * | 3/2004 | Pillai et al. | | 378/196 |
| 2005/0197559 A1 * | 9/2005 | Boese et al. | | 600/407 |
| 2005/0254628 A1 * | 11/2005 | Saladin et al. | | 378/197 |
| 2006/0058645 A1 * | 3/2006 | Komistek et al. | | 600/424 |
| 2008/0177280 A1 * | 7/2008 | Adler et al. | | 606/130 |
| 2009/0082660 A1 * | 3/2009 | Rahn et al. | | 600/411 |

OTHER PUBLICATIONS

Bey, M., Zauel, R., Brock, S., Tashman, S. Validation of a New Model-Based Tracking Technique for Measuring Three-Dimentional, In Vivo Glenohumeral Joint Kinematics. ASME. vol. 128. Aug. 2006. 604-609.

You, B., Siy, P., Anderst, W., Tashman. In Vivo Measurement of 3-D Skeletal Kinematics from Sequences of Biplane Radiographs: Application to Knee Kinematics. IEEE Transactions on Medical Imaging. vol. 20, No. 6. Jun. 2001. 514-525.

International Search Report and Written Opinion for PCT Patent Application No. PCT/US2008/77605, mailed Nov. 28, 2008, 10 pages.

* cited by examiner

A. Alternating Exposures
(conventional biplane imaging)

B. Simultaneous Exposures
(Current dynamic biplane imaging scheme)

C. Offset Exposures
(Proposed scatter reduction imaging scheme)

BI-PLANE X-RAY IMAGING SYSTEM

CLAIM OF PRIORITY UNDER 35 U.S.C. §119

The present Application for Patent claims priority to Provisional Application No. 60/975,417 entitled BI-PLANE X-RAY IMAGING SYSTEM filed Sep. 26, 2007, and assigned to the assignee hereof and hereby expressly incorporated by reference herein.

BACKGROUND

The present disclosure relates to radiographic imaging and in particular to an apparatus and method for positioning two bi-plane imaging systems that facilitates three-dimensional measuring of in vivo joint kinematics.

Cartilage is the part of the joint that cushions the ends of the bones and allows joints to move freely. Osteoarthritis (OA) is considered to be one of the most common forms of arthritis. OA is referred to in the medical industry by many different names, including degenerative joint disease, osteoarthritis, hypertrophic arthritis and degenerative arthritis. Generally, OA refers to a chronic condition portrayed by the breakdown of the cartilage within a joint. The breakdown of cartilage causes friction between the bones, causing stiffness, pain and loss of movement in the joint.

Today, it is estimated that over 20 million Americans are plagued by the effects of OA. Additionally, OA accounts for approximately a quarter of visits to primary care physicians as well as about half of all non-steroidal anti-inflammatory drugs (NSAID) prescriptions. It has been estimated that over 75% of the population can have radiographic evidence of OA by the age of 65, although only 50-60% of those can be symptomatic. Most often, treatment is with NSAIDs, local injections of glucocorticoid or hyaluronan. In severe cases, patients can undergo surgery with joint replacement or fusion.

Despite the disease's prolonged existence and rate of recurrence, its cause is still not completely known by the medical industry. As such, there is no cure. However, it is believed that there are a number of defined factors that contribute to OA. These factors include enhanced age, obesity, injury, overuse and genetics.

As with many diseases, there are several stages in which the body (and joints) undergo. First, cartilage can lose elasticity which inherently makes it more easily damaged by injury or overuse. Another stage occurs when the wear of the cartilage causes changes to underlying bone. When this occurs, the bone can thicken and cysts may occur under the cartilage. Spurs or osteophytes develop near the end of the bone at the affected joint. This breakdown of the cartilage can cause bits of bone or cartilage to 'float' loosely in the joint space. As a result, the joint lining, or the synovium, usually becomes inflamed due to cartilage breakdown causing cytokines (or inflammation proteins) and enzymes that further damage cartilage.

Essentially, changes in the cartilage and bones of the joint can lead to pain, stiffness and range of motion limitations. Deterioration of cartilage can affect the shape and makeup of the joint thereby prohibiting or impairing 'normal' function. In other words, deterioration of cartilage in a knee or ankle joint can cause a person to limp. As well, in a more extreme case, fragments of the bone and/or cartilage can 'float' within the joint. Here, the person can experience pain when putting weight on the joint (e.g., standing, walking, ascending/descending stairs, etc.). As the bone surfaces become less protected by cartilage, a patient can experience pain upon weight bearing. Due to decreased movement because of the pain, regional muscles may waste away or atrophy.

OA (and other joint impairment) diagnosis is normally accomplished via imaging techniques or X-rays. This is possible because loss of cartilage, narrowing of the joint space between the bones, and bone spur formation (aka osteophytes) can be easily detected by way of X-rays. With or without other techniques, such as MRI (magnetic resonance imaging), arthrocentesis and arthroscopy, diagnosis can be made by a careful study of the duration, location, the character of the joint symptoms, as well as, the appearance of the joints themselves. Unfortunately, to date, there are no reliable and effective mechanisms available to detect OA in its early and potentially treatable stages.

Conventional approaches for measuring three-dimensional (3D) joint position and motion have relied upon cadaveric simulations, two-dimensional (2D) imaging, static 3D imaging, conventional motion measurement systems, and invasive techniques using bone pins. Unfortunately, there are significant limitations associated with each of these approaches. Cadaveric experiments can provide highly accurate measures of joint position or motion, but are unable to accurately duplicate the complex motions, muscle forces, or joint forces associated with dynamic in vivo conditions. Joint position has been evaluated radiographically, using fluoroscopy to measure dynamic joint motion or plane films to measure static joint position. However, these 2D assessments of joint motion cannot sufficiently characterize motion of a joint that is capable of translating in three directions and rotating about three axes. Static 3D imaging of joint position has been performed with magnetic resonance imaging, CT, or biplane radiography, but these techniques are currently incapable of assessing dynamic joint motion. Conventional motion measurement systems have used video cameras to measure the position of surface markers or anatomical landmarks or have relied on surface-mounted electromagnetic motion sensors. Combinations of the aforementioned approaches are also used, with Barnett and colleagues describing the combined use of a surface-mounted scapular locator, electromagnetic device, and optical motion tracking system. Skin-mounted sensors are highly susceptible to skin movement artifact, and their reliability for the accurate assessment of joint kinematics has not been established. Invasive techniques using bone pins have been used by McClure and colleagues to directly measure scapular motion of eight volunteers. However, this invasive approach not only limits the number of willing volunteers, but also makes serial studies over time impractical since bone pins cannot be reliably secured in the same location. More recently, our laboratory has begun using dynamic radiostereometric analysis (RSA) to measure 3D joint kinematics by tracking the position of implanted tantalum beads with a novel, high-speed, biplane X-ray system. This approach has been used extensively to study in vivo knee kinematics in canines and humans. However, tantalum marker implantation is an invasive procedure and therefore is limited to only those subjects who are undergoing a surgical procedure.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

The innovation disclosed and claimed herein, in one aspect thereof, comprises a system that facilitates examination of a subject using high-speed, three-dimensional (3D) motion analysis at extremely high resolution. More particularly, the system enables examination of the subject on two different planes (aka 'bi-plane') which effects high speed 3D imaging of skeletal motion. In operation, a subject can walk or run (e.g., on a treadmill or other apparatus), jump, throw, twist, bend, etc. while the motion is captured by a biplane X-ray system and high-speed video cameras. It can be understood that the bi-planar images captured by the system can be used in combination with the precise definition of geometry provided by CT (computed tomography) scans, for example, to reconstruct individual-specific motion of nearly any joint in the body.

In one aspect, an apparatus provides for dynamic radiographical imaging. A first support structure comprises a first source arm that positions a first radiological imaging source at a first source position and comprises a first imaging arm that positions a first radiological imaging receiver at a second imaging position selected for radiological imaging on a first axis passing through a selected portion of a subject. A second support structure comprises a second source arm that positions a second radiological imaging source at a third source position and comprises a second imaging arm that positions a second radiological imaging receiver at a fourth imaging position selected for radiological imaging along a second axis intersecting the first axis and passing through the selected portion of the subject. Position references that are coupled between the first and second support structures determine relative orientation between the first and second axes. An imaging system generates three-dimensional radiology imaging data dynamically changing as the subject moves by processing bi-planar radiological imaging data received from the first and second imaging receivers In another aspect, an apparatus supports two biplane radiographic imaging systems used to obtain a dynamic three dimensional radiological imaging. A gantry pivoting hub assembly has an upper sleeve that supports a first beam and a lower sleeve that supports a second beam. The first and second sleeves are attached for horizontal rotation relative to each other and a support surface. A first telescoping originating arm is attached to translate on one end of the first beam and terminates in a vertically pivoting attachment for a radiological source. A first telescoping receiving arm is attached to translate on another end of the first beam and terminates in a vertically pivoting attachment for a radiological receiver. A second telescoping originating arm is attached to translate on one end of the second beam and terminating in a vertically pivoting attachment for a radiological source. A second telescoping receiving arm is attached to translate on another end of the second beam and terminates in a vertically pivoting attachment for a radiological receiver. The second beam is shorter than the first beam to allow alignment of the first and second beams with the first telescoping originating and receiving arms positionable to avoid contacting the second beam.

In a further aspect, a method provides for adjusting connected supporting structures that position biplane radiological imaging components whose adjustable imaging axes intersect through a selected portion of a subject. A relative orientation is determined between the adjustable imaging axes based upon the adjustable connected supporting structures, wherein the adjustable imaging axes are vertically adjustable down to 0 degrees relatively and horizontally adjustable down to 0 degrees.

To the accomplishment of the foregoing and related ends, the one or more aspects comprise the features hereinafter fully described and particularly pointed out in the claims. The following description and the annexed drawings set forth in detail certain illustrative aspects of the one or more aspects. These aspects are indicative, however, of but a few of the various ways in which the principles of various aspects can be employed and the described aspects are intended to include all such aspects and their equivalents.

DETAILED DESCRIPTION

Figure 1:
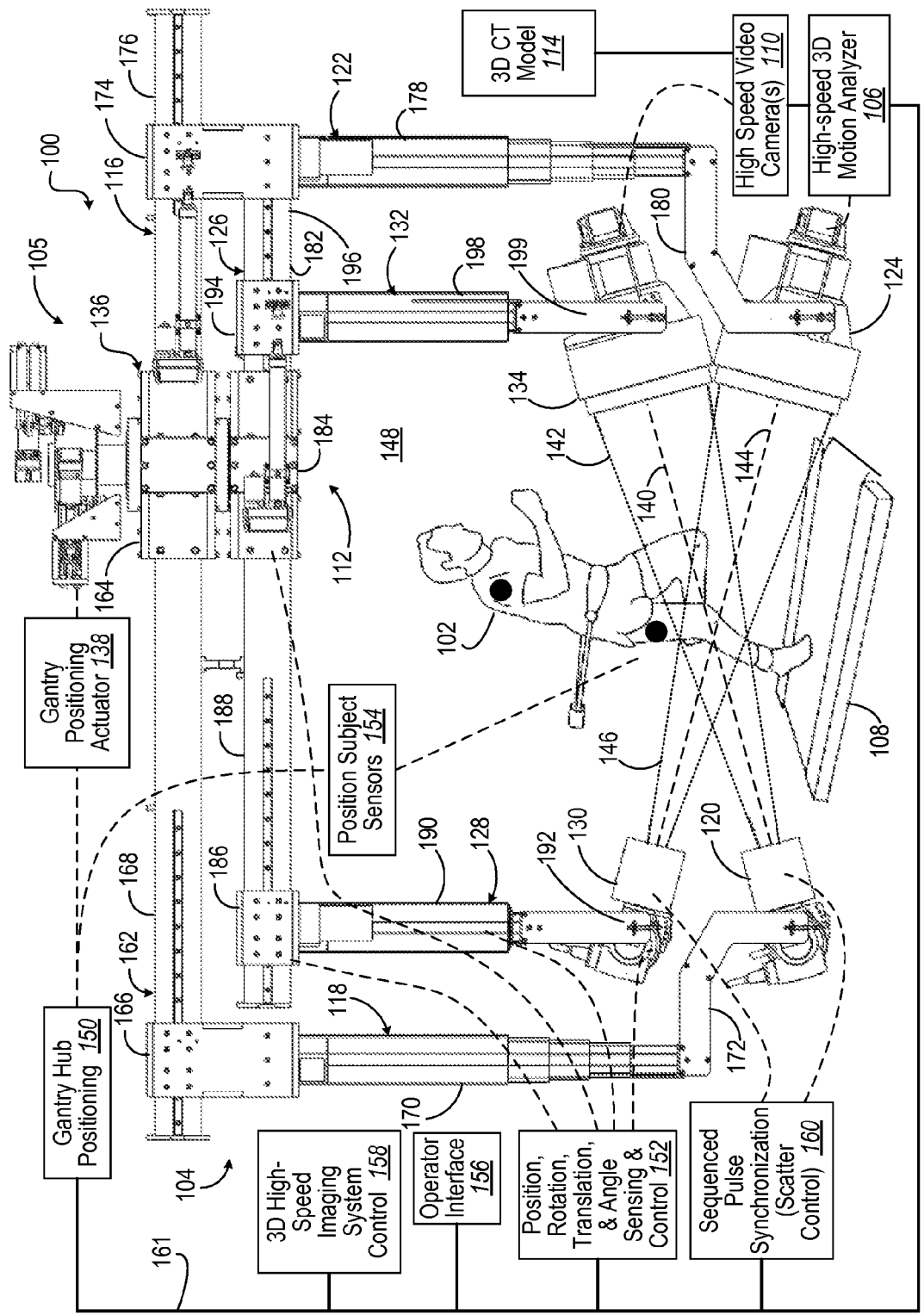
FIG. 1 is a front view of a gantry system with overhead support omitted and other portions of a high speed cineradiography system depicted in a block diagram.

With reference to FIG. 1, a high speed cineradiography system 100 facilitates examination of a subject 102 using high-speed, biplane X-ray apparatus 104, supported by a gantry system 105, analyzed by three-dimensional (3D) motion analyzer 106 at very extremely high resolution with two different planes (aka 'bi-plane'), which effects high speed 3D imaging of skeletal motion. A subject 102 can walk or run (e.g., on a treadmill 108 or other apparatus) or perform a variety of movements of nearly any joint in the body while the motion is captured by the biplane X-ray system 104 and high-speed video camera(s) 110. The treadmill 108 can be instrumented, such as with speed information and force sensing to assist in manually or automatically selecting a point in the motion of the subject that is of interest. For example, a right knee joint can be under evaluation and information is desired for when the knee reaches a peak force at a particular point in a running stride or walking stride that can be determined as a function of maximum force and optimal speed range. Other sensors (e.g. photocells, proximity sensors, pressure sensors, accelerometers, electromyography) could also be used to intitiate imaging based on position, movement initiation or muscle force generation. These sensing modalities are especially applicable to motions of the spine and upper extremities.

A nested pair of pivoting, telescoping and translating gantry imaging arms 112 of the gantry system 105 enhances positioning and sensing of position to achieve desired orientations. Model-based tracking approach performed by the 3D motion analyzer 106 represents a non-invasive technique for accurately measuring dynamic joint motion that does not require invasive techniques. The bi-planar images captured by the high-speed video camera(s) 110 can be used in combination with the precise definition of geometry provided by CT (computed tomography) scans, depicted as a 3D CT model 114, or other imaging modality to reconstruct individual-specific joint motion. Systems of computational evaluation of joint motion and function are thereby enabled through the use of high speed cineradiography.

Essentially, the innovation discloses systems of computational evaluation of joint motion and function through the use of high speed cineradiography, which enables in-vivo evaluations of, but not limited to, knees, shoulders, spine, hips, and ankles and feet. In doing so, joint biomechanics using high-speed bi-planar radiography are employed. It is to be understood that the subject innovation relates to a bi-plane X-ray imaging system that can provide for simultaneous viewing of an object in two planes. It can further be understood that is bi-plane viewing enables a three-dimensional (3D) orientation of the target subject 102.

The exemplary nested pair of pivoting, telescoping and translating gantry arms 112 provides a first support structure 116 comprising a first source arm 118 for positioning a first radiological imaging source 120 and a first imaging arm 122 for positioning a first radiological imaging receiver 124. A second support structure 126 comprising a second source arm 128 for positioning a second radiological imaging source 130 and a second imaging arm 132 for positioning a second radiological imaging receiver 134. A gantry pivoting hub assembly 136 supports the first and second support structures 116, 126 and can be supported by floor mounting or ceiling mounting (not shown in FIG. 1).

Gantry positioning actuator controls 138 that positions the nested pair of pivoting, telescoping and translating gantry arms 112 either sense the position of each constituent actuator or have sufficient certainty of position based on its forward control loop of some or all of its consistent actuators in order to determine the relative and absolute orientation thereof. Thus, a first axis 140 of a first plane cineradiological beam 142 supported by the first support structure 116 can be determined with respect to a second axis 144 of a second plane cineradiological beam 146 supported by the second support structure 126.

The gantry positioning actuator controls 138 can further provide absolute positioning information within a room 148, such as by gantry hub positioning actuators 150 that move the gantry pivoting hub assembly 136, such as in one or two horizontal directions. To that end, a position, rotation, translation and angle sensing control 152 senses, calculates or otherwise determines certain positions of the nested pair of telescoping and translating gantry imaging arms 112. Advantageously, patient position sensors 154 detect a position of the subject 102 within the room 148, enabling adjustments by the gantry hub positioning actuators 150 to maintain the two axes 140, 146 relative to the subject 102. For example, an operator can use an operator interface 156 to make settings of a 3D high-speed cineradiological system control 158, such as setting the axes 140, 146 with a desired orientation, including a relative vertical and horizontal angle there between, as well as desired orientation with respect to the room 148 and the subject 102. The cineradiological system control 158 can also enable a sequenced pulse synchronization component 160 that ensures that the first and second radiological imaging sources 120, 130 emit short duration pulses such that each radiological image obtained thereby are not blurred by motion of the subject 102. In addition, these pulses are closely synchronized so that a correlation can be made of these two planes to determine a dynamic three-dimensional cineradiological image. Advantageously, the pulses are additionally closely sequenced so that Compton scattering to the other radiological imaging receiver 134, 124 is avoided. These electronic controls and analyzers 106, 156, 152, 158, 160 can communicate via a communication path 161 comprising a bus or network.

A high degree of position adjustability is provided in the exemplary aspect, although it should be appreciated with the benefit of the present disclosure that some applications can omit one or more these adjustment capabilities or substitute an equivalent adjustment means. The first support structure 116 comprises a first horizontal beam 162 fixed within an upper rectangular sleeve 164 that allows rotation of the beam via the gantry pivoting hub assembly 136. The first source arm 118 comprises an upper guide 166 that can translate horizontally along a long end 168 of the first horizontal beam 162. A telescoping vertical portion 170 of the first source arm 118 allows a height of the first radiological imaging source 120 to be changed. An extended arm bracket 172 at a termination of the telescoping vertical portion 170 allows the imaging source 120 to be pivoted in vertical azimuth. The first imaging arm 122 comprises an upper guide 174 that can translate horizontally along a short end 176 of the first horizontal beam 162. A telescoping vertical portion 178 of the first imaging arm 122 allows a height of the first radiological imaging receiver 124 to be changed. An extended arm bracket 180 at a termination of the telescoping vertical portion 178 allows the imaging receiver 124 to be pivoted in vertical azimuth.

The second support structure 126 comprises a second horizontal beam 182 fixed within a lower rectangular sleeve 184 of the gantry pivoting hub assembly 136. The second source arm 128 comprises an upper guide 186 that can translate horizontally along a long end 188 of the second horizontal beam 182. A telescoping vertical portion 190 of the second source arm 128 allows a height of the second radiological imaging source 130 to be changed. An arm bracket 192 at a termination of the telescoping vertical portion 190 allows the imaging source 130 to be pivoted in vertical azimuth. The second imaging arm 132 comprises an upper guide 194 that can translate horizontally along a short end 196 of the second horizontal beam 182. A telescoping vertical portion 198 of the second imaging arm 132 allows a height of the second radiological imaging receiver 134 to be changed. An arm bracket 199 at a termination of the telescoping vertical portion 190 allows the imaging receiver 134 to be pivoted in vertical azimuth.

For clarity and to show a particular advantageously arrangement, the axes 140, 144 of FIG. 1 are vertically aligned with the gantry pivoting hub assembly 136 aligning the upper and lower cylindrical sleeves 164, 184. Thus, it is convenient that the imaging receivers 124, 134 from the other support structure 116, 126 be used to complete the respective axes 140, 144 with the imaging sources 120, 130. Later configurations depict a pivotal displacement (horizontal angle) between the first and second support structures 116, 126 with the axes 140, 144 thus terminated at the imaging receiver 124, 134 that shares the same beam 162, 182. For applications that do not require a horizontal angle between beams axes 140, 144, one pair of arms or side wall mounting could be implemented. However, this vertical stacking is flexibly enabled in the illustrative aspect as well as other arrangements described below.

Figure 2:
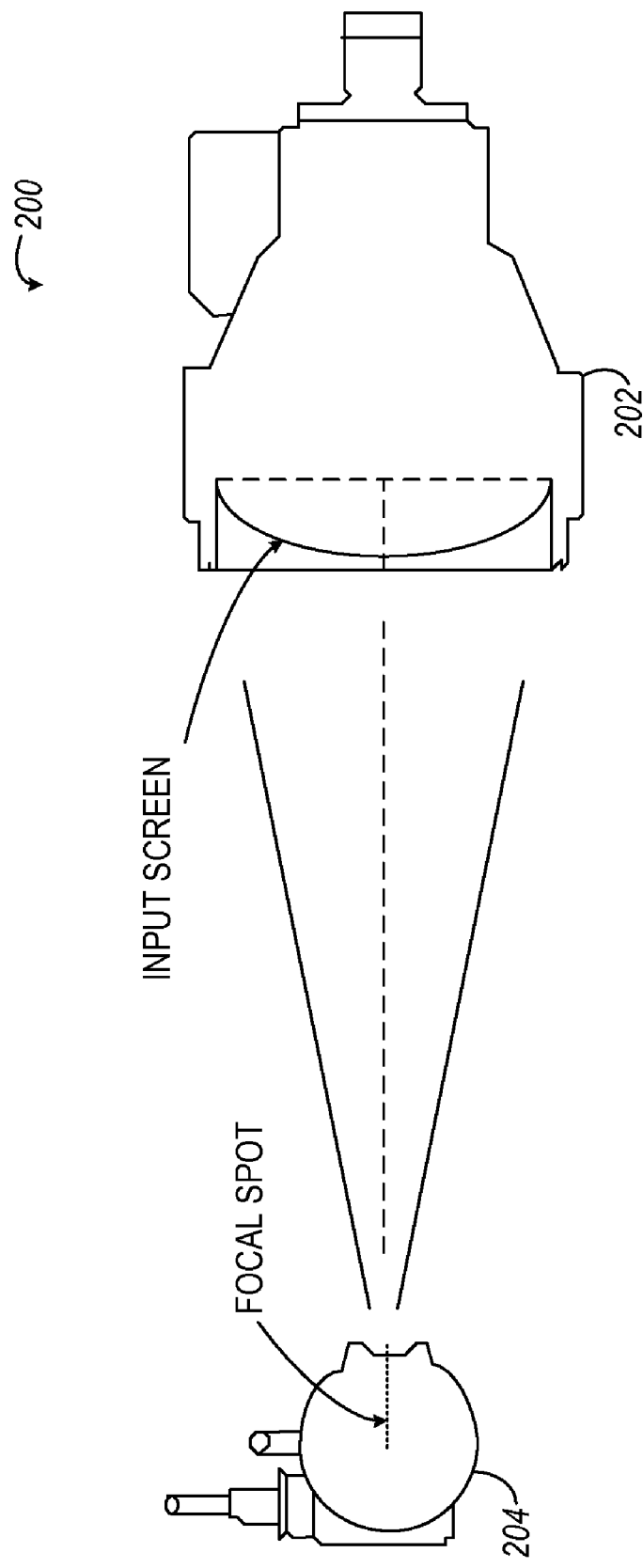
FIG. 2 is a diagram of an imaging source and imaging receiver of the high speed cineradiography system.

With reference to FIG. 2, the degree of pivoting is coordinated with the amount of telescoping and translation so that the imaging source 120, 130 aligns with one of the imaging receivers 124, 134 to achieve one plane cineradiography, as depicted at 200. In an exemplary aspect, the imaging receivers 124, 134 comprise 16" image intensifiers 202 and the imaging sources 120, 130 comprise X-ray tubes with collimators 204. It can be appreciated that the movements of the image intensifiers 202 and X-ray tubes 204 can be application specific and set as desired or appropriate.

As described above, the high-speed bi-plane radiography system 104 (FIG. 1) enables in-vivo assessment of joint function. The bi-plane radiography system 104 is capable of acquiring stereo-pair radiographic images at rates from at least 30 to 1000 frames per second of nearly any motion or joint. As shown in the figures attached, the radiographic equipment can be mounted in the gantry system 105 that provides adequate positioning flexibility for imaging the different joints of the body, along with an imaging area large enough for a variety of dynamic activities (walking, running, jumping, throwing, etc.). Three-dimensional bone positions can be determined using software applications developed for matching the bones in the X-ray images with 3D models developed from subject-specific CT scans. This system can provide accurate (±0.1 mm) assessment and direct 3D visualization of dynamic joint function, and can overcome the limitations of conventional gait or motion analysis.

By incorporating the latest imaging technologies, the subject X-ray system has considerably enhanced capabilities, including greater resolution, larger field of view and better overall image quality. One of the most significant advancements is in the unique configuration of the custom-designed gantry system as shown in the figures attached. This custom-designed gantry system can provide dramatically better flexibility for positioning the imaging hardware. These enhancements can enable an even wider range of applications for this versatile imaging technology. Unlike systems with stand-alone sources and/or detectors, the pivoting arm structure provides this flexibility while facilitating accurate alignment of the x-ray sources and detectors.

In an illustrative aspect, inner and outer X-Ray generators (not shown) perform high-power pulsed cineradiography, which in the illustrative implementation entails 1 ms pulse width, 125 Hz minimum at up to 320 mA, 90 kVp. At frequencies up to 60 Hz, imaging pulse width generated is 1-16 ms with power levels up to 500 mA, 90 kVp. The imaging pulses have rapid rise/fall times (e.g. <200 μs). The two X-ray generators support simultaneous biplane firing, which can be deconflicted for scatter control but closely sequenced for close correlation in time when creating a three-dimensional model of the imaged structure. The X-ray generators have radiographic mode (continuous) up to 100 kW and a high power/HU 0.3/0.6 mm spot-size tube. In an exemplary embodiment, the inner and outer X-ray generator are Model CPX3100CV SP available from EMD Technologies, with special firmware modification to provide operation to greater than 125 frames per second. X-ray tubes are model G1080/B-160 available from Varian Medical Systems of Palo Alto, Calif. Each have beam limiting device model R302A available from Ralco S.R.L. of Biassono, Italy.

Inner and outer image intensifiers each have a 40 cm high contrast tube, produce a minimum of 40 lp/cm resolution with fast output phosphor (e.g. P20; <1 ms decay time) and are tolerant of high exposure levels. Optical coupling is made to an external imaging camera (not shown). Alternatively, a flat-panel detector can be used that meets or exceeds exemplary specifications of 40×40 cm field of view (FOV), 0.25 mm pixel pitch, 200 frames/s, and 12-bit dynamic range. In an exemplary implementation, the image intensifiers 124, 134 are Model TH 9447QX H694 L VR70 available from Thales/DiaMed. This image intensifier provides an entrance field size (nominal) of 360/290/215 mm (16 inch), an output image diameter of 35 mm, central resolution minimum of 46/50/56 line pair per mm (lp/mm), system resolution limited by CCD matrix, contrast ratio minimum of 20:1 in 16 inch mode, conversion factor minimum of 350 cd.m-2/mR.s-1, detective quantum efficiency of 65 at 59.5 keV. Anti-scatter grids are employed at the face of the image intensifiers to reduce scatter and improve image quality. A photomultiplier tube is employed with an objective lens of 100 mm, a right angle optics cube, a standard dovetail camera mount for camera mounting in 90° positions. Lens Focus and iris adjustment is provided with an ability to adjust without removing the camera, which may be accomplished either by a manual or motorized scheme. Visual access can be provided to observe the f-stop setting.

Translation and rotation of the inner and outer arms provides for biplane imaging, 45-135° adjustable inter-beam angle, a source-detector distance 160-220 cm, 2.5 m overhead clearance, imaging height adjustable from floor to 2 m, beam inclination angle adjustable from −30° to +30°, and open path through system for running, treadmill, etc.

Image intensifiers 202 and digital video cameras 110 could be replaced with digital flat panel X-ray detectors (not shown). Flat panel detectors offer the potential for higher image quality, lower radiation exposure and larger fields of view. They are also lighter, so their use could reduce structural demands on the gantry system, which can enable reduced design cost and complexity.

Figure 3:
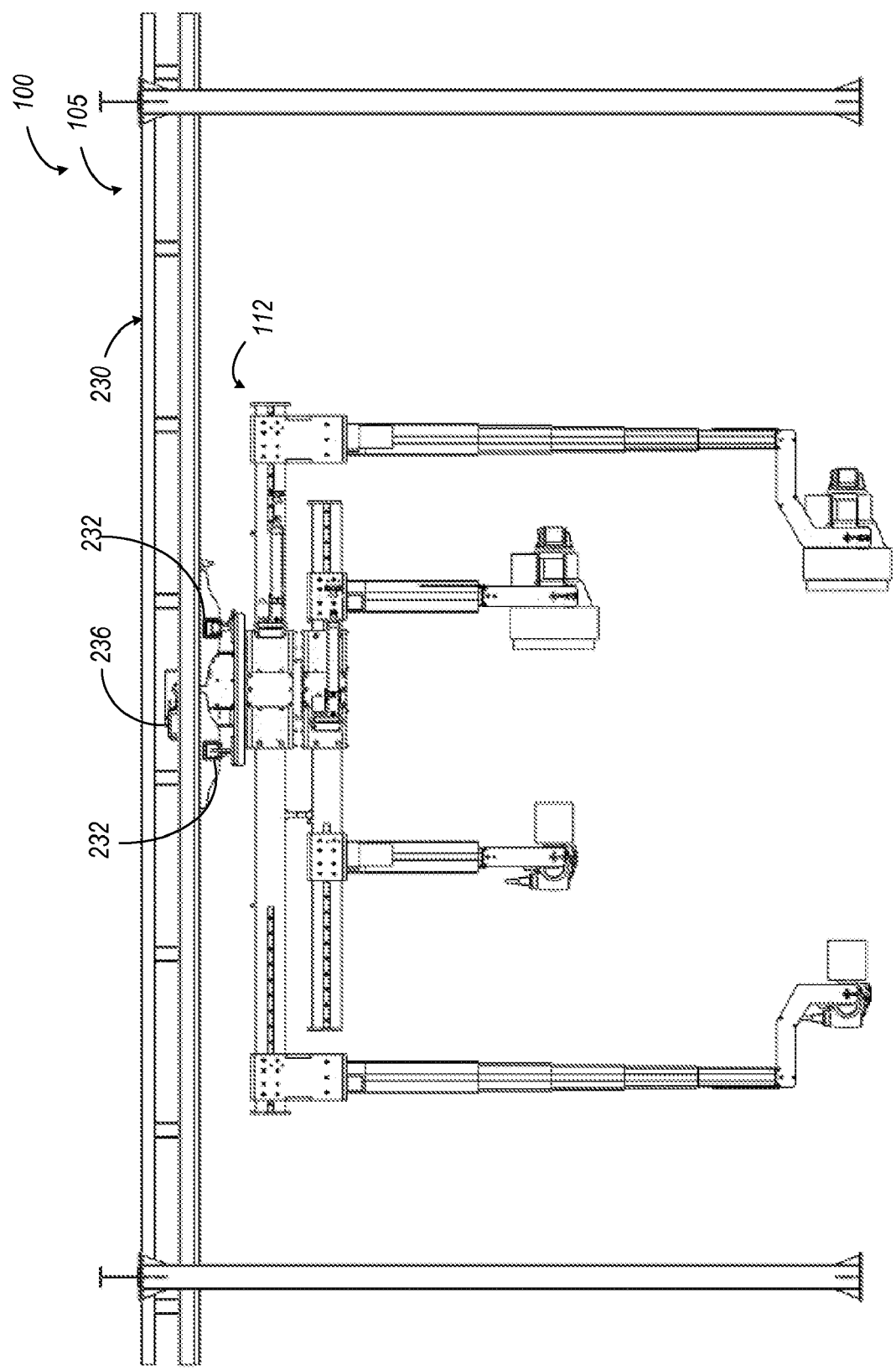
FIG. 3 is a front view in elevation of the gantry system including overhead support.
Figure 4:
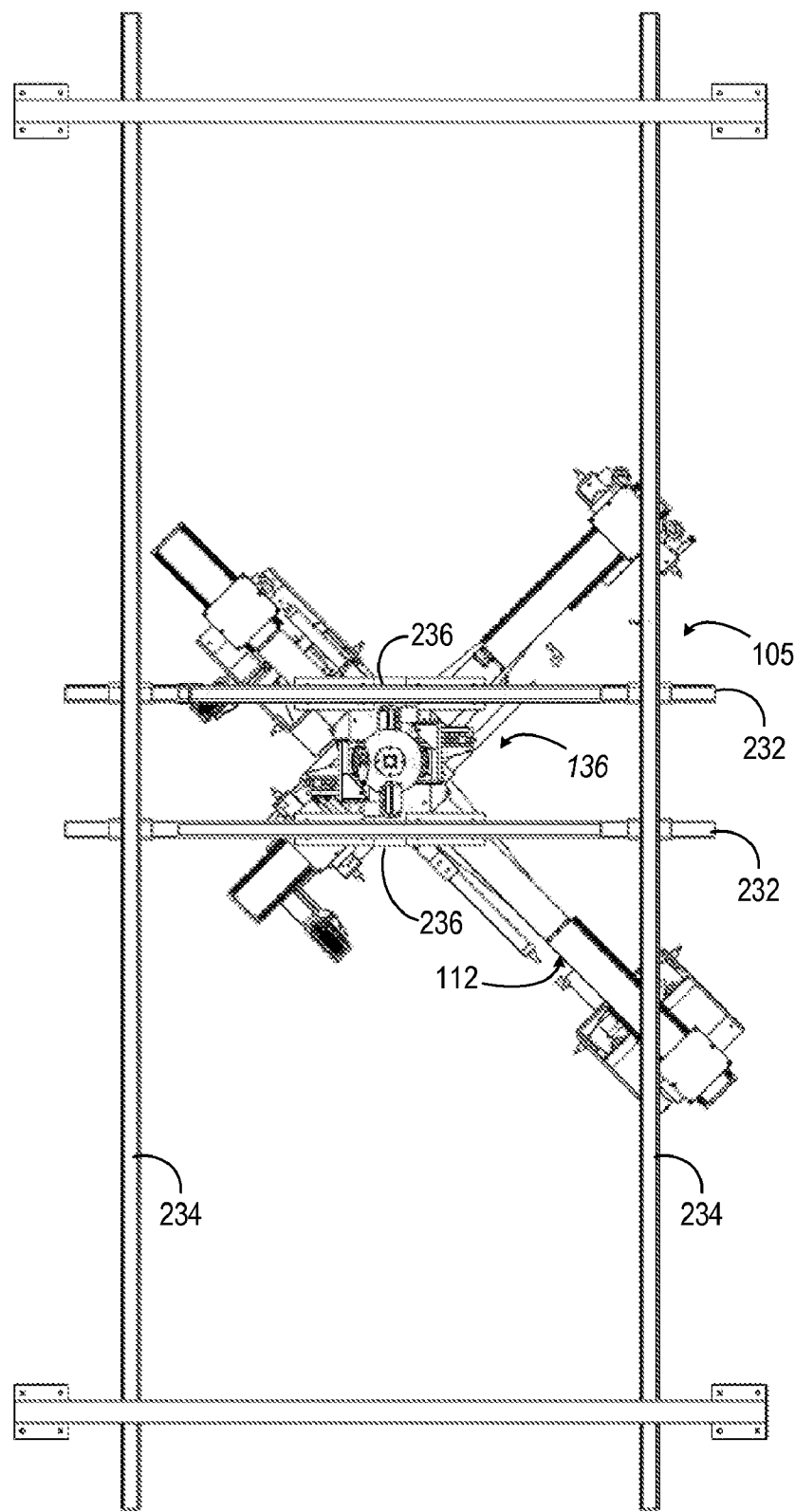
FIG. 4 is a top view of the gantry system of FIG. 3.

In FIGS. 3-4, overhead structure 230 of the gantry system 105 includes a pair of movable transverse rails 232 upon which the gantry pivoting hub assembly 136 can transversely translate. A pair of fixed longitudinal rails 234 that are orthogonal to the transverse rails 232 support the transverse rails 232 for longitudinal translation. Transverse and longitudinal motor-driven gantry positioning and motion tracking components 236 can make these positioning automatic or powered. The overhead structure 230 from which the pivoting arms 112 are suspended provides freedom of movement in two directions to enable free positioning of the gantry system 105 anywhere within the track footprint (i.e., limited only by size of the imaging room 148). In one aspect, roller bearing trucks provide movement. Gantry position can be adjusted manually, and locked in place by lever clamps. Alternatively, motorized control of truck position can be used, such as incorporating a belt, chain, worm-drive or similar system (not shown), enhancing reconfiguration efficiency. Thus, by combining the motor-driven positioning with sensors (ultrasonic or video-based) for detecting subject position and a suitable control system, it would also be possible to have the X-ray system "follow" the subject during the desired movement to keep the joint of interest in the imaging field of view for a longer period of time.

Figure 5:
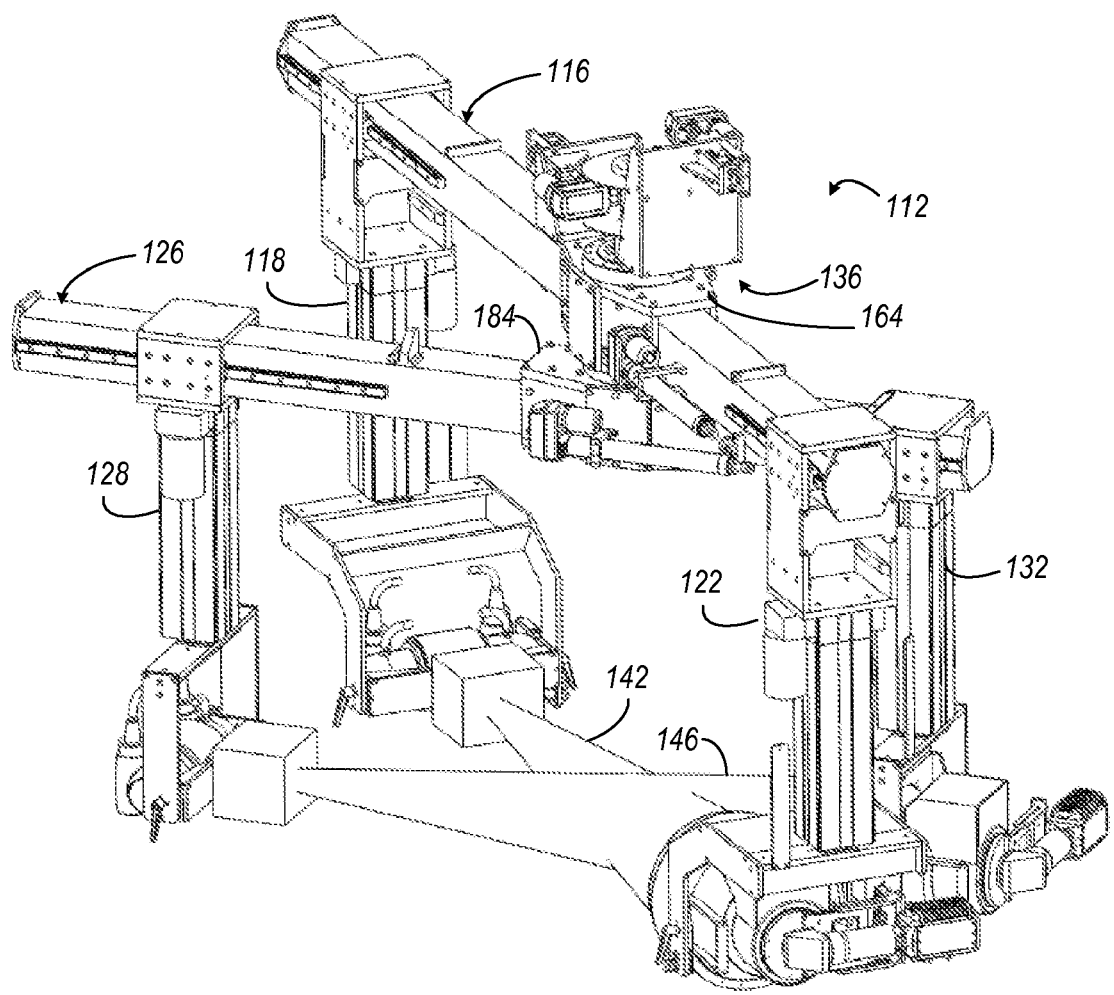
FIG. 5 is an isometric view from above of the gantry system positioned with each telescoping arm fully raised, the first and second support structures rotated to a relative horizontal angle of about 45°.
Figure 6:
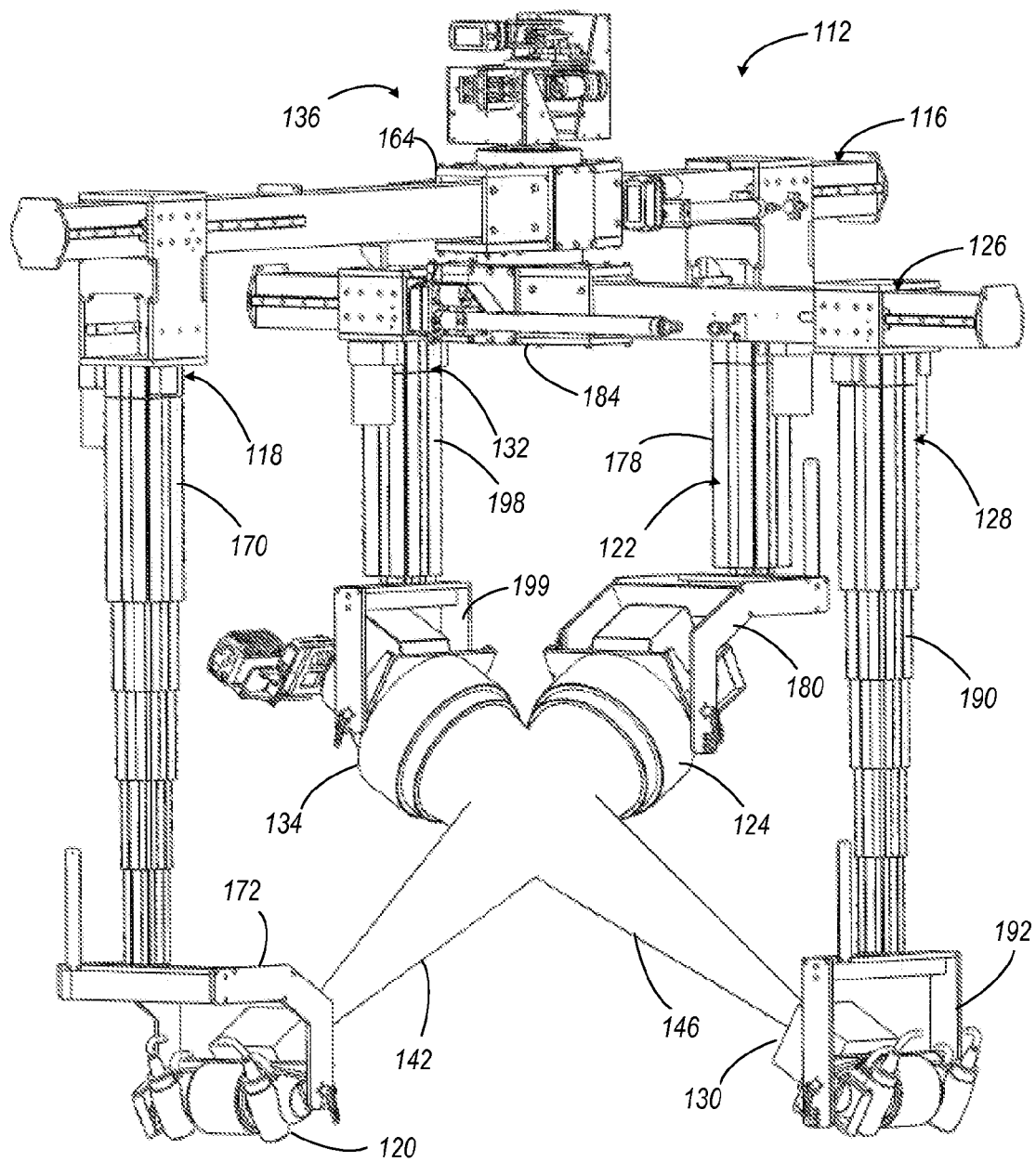
FIG. 6 is an isometric view of the gantry system as depicted in FIG. 5 but with the imaging arms fully extended angle 90° tilt 30° sources lowest detector highest with corresponding pivoting of the arm brackets.

Repositioning can approach certain portions of the subject's body in angles that achieve the desired results. In FIG. 5, the gantry system 105 has been positioned with the telescoping portions 170, 178, 190, 198 of the respective arms 118, 122, 128, 132 full raised such that the relative vertical angle in the beams 142, 146 is 0° and a horizontal angle in the beams 142, 146 is 45°. As another example, in FIG. 6, the telescoping portions 170, 190 of the source arms 118, 128 have been lowered to their lowest height with the arm brackets 172, 180, 192, 199 appropriately swiveled to achieve beam 142, 146.

Figure 7A:
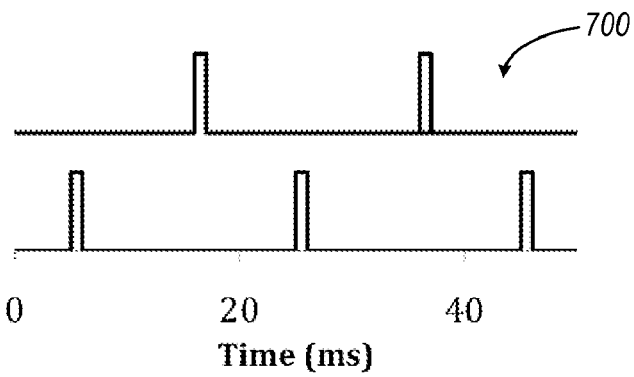
FIG. 7A is a plot of conventional sequence of pulses.
Figure 7B:
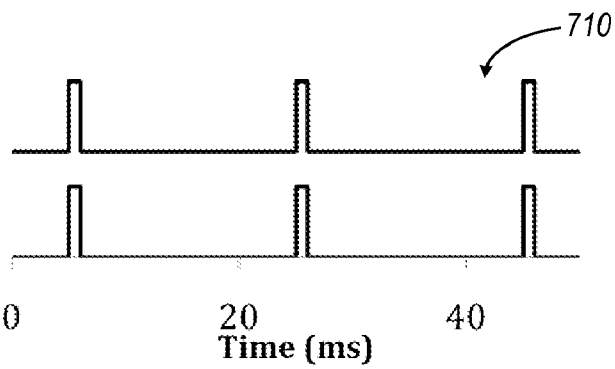
FIG. 7B is a plot of simultaneous biplane pulses for time correlation.

In FIGS. 7A-7B, pulse sequencing is depicted for optimizing image quality during simultaneous biplane radiographic image acquisition. In particular, methodology suggested thereby is for reducing effects of X-ray scatter. A technique can significantly improve image quality during biplane radiographic imaging for 3D motion measurement. Radiographic image quality can be degraded by Compton scattering, which occurs when X-ray photons strike electrons along the path between the X-ray source and image detector. Scattered radiation degrades image contrast and quality, and increases with the volume and thickness of tissues within the X-ray beam. Scatter is especially problematic for biplane imaging, because the radiation scattered from one image plane creates noise in the other plane. For this reason, clinical biplane imaging systems, e.g. for cine-angiography, alternate X-ray generation/acquisition between the two imaging planes so that scatter from one plane does not appear in images from the other. The best commercially available systems typically acquire images at 50 or 60 frames/s (16.67 or 20 ms/frame), with a ½ frame offset between the two images, using short (1 ms) pulses to eliminate blur as depicted at 700 in FIG. 7A. Since these systems are designed for visualization (not quantitative measurement), the offset between views is acceptable.

For biplane imaging systems designed for quantitative, 3D motion measurement, this delay would generally be unacceptable, since the techniques that match a pair of 2D views to a 3D position require that the views be acquired at the same instant. If the bone being tracked moves significantly in between acquisitions, tracking accuracy and reliability is seriously degraded. Most applications described for dynamic biplane imaging have targeted lower-extremity function, where movement speeds can be quite high. For these applications, simultaneous imaging is employed for 3D tracking accuracy (50 Hz example as depicted at 710 of FIG. 7B; timing is similar for frame rates up to 180 Hz). In most cases, scatter can be reduced to manageable levels by using conventional anti-scatter grids, due to the relative low volume of tissue in the imaging field (resulting in correspondingly low levels of beam-to-beam scatter).

In one aspect, a biplane imaging system has been specifically designed for application to joints and movements beyond lower extremity function. Some joints/movements (e.g. hip, lumbar spine) involve much slower movement speeds as well as much greater tissue volume in the imaging field. Simultaneous imaging creates very high levels of scatter which seriously degrade image quality. Conventional anti-scatter grids are insufficient to eliminate the problem.

Figure 7C:
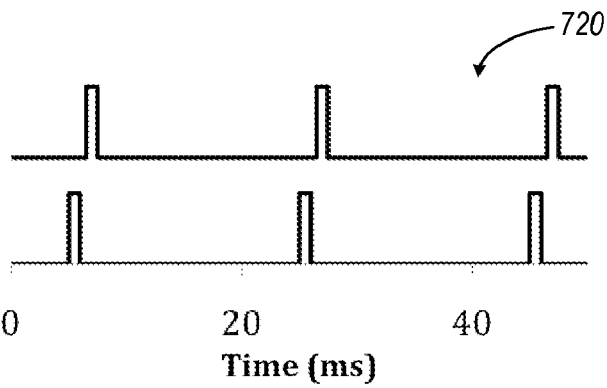
FIG. 7C is a plot of closely sequenced alternating biplane pulses for close time correlation without Compton scattering.
Figure 8:
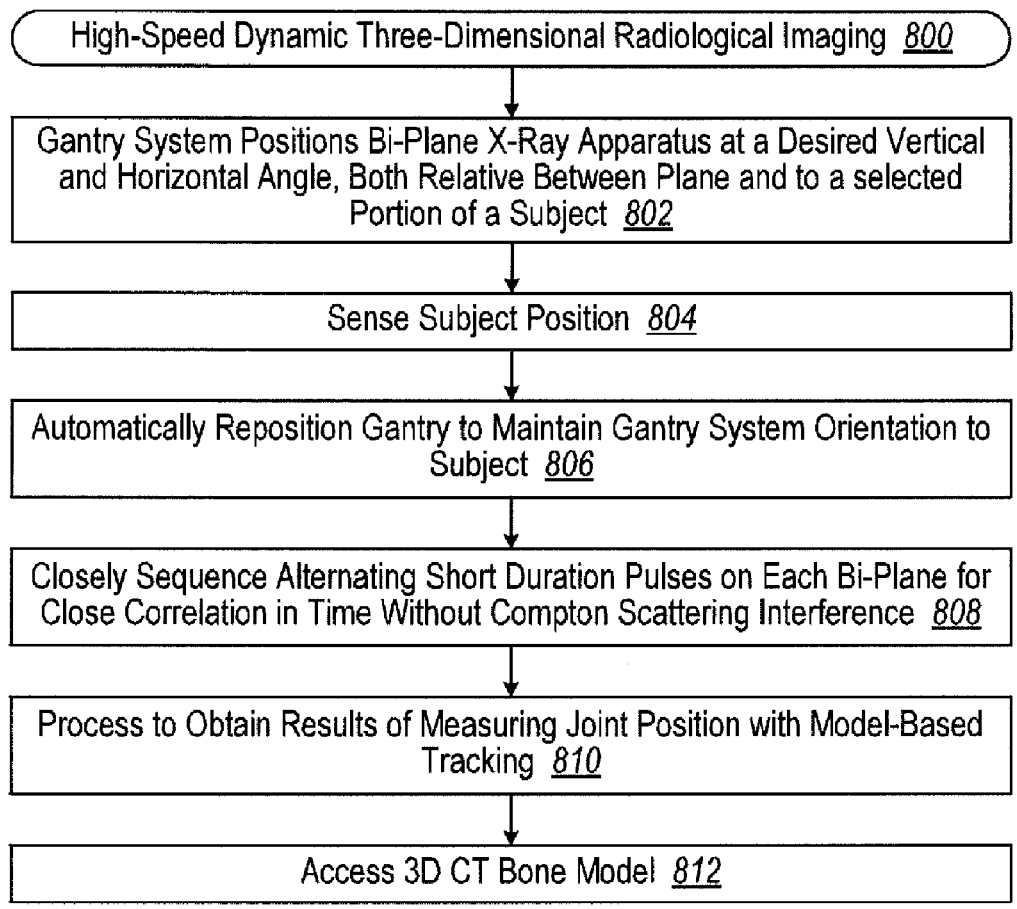
FIG. 8 is a flow diagram for a methodology for high-speed biplane radiographic imaging.

A new timing scheme can avoid this problem for biplane imaging of moderate-speed, high-volume joints/movements (e.g. hip, lumbar spine). It differs from typical biplane applications of FIG. 7A in that the delay between the termination of one generator pulse and the initiation of the other pulse is minimized. This would be accomplished by using a precision pulse/delay generator (e.g. Berkeley Nucleonics Corp. Digital Delay-Pulse Generator, model number 565) to trigger the second generator after a delay of slightly more than the pulse width relative to the first generator, as shown at 720 in FIG. 7C (e.g., frame rates 15-150 Hz, and more particularly 50 Hz). This would create a pair of near-simultaneous images free of beam-to-beam scatter. For slow to moderate movement speeds, the short time delay between images would have a minimal effect on 3D tracking accuracy. For faster movements, software compensation could be employed to account for bone movement between the two images.

In use, a methodology 800 for high-speed biplane radiographic imaging is flexibly configured with a gantry system that can position bi-plane X-ray apparatus at a desired vertical and horizontal angle, both relative to each plane as well as to a selected portion of a subject. The radiographic imaging system consists of a support system capable of positioning the X-ray tubes and image intensifiers in a variety of configurations and positions (block 802). In an illustrative aspect, a high-speed radiographic system consists of two X-ray systems, each with a 100 kW constant-potential high-frequency cardiac cine-radiographic generator (EMD CPX-3100CV), a 0.3/0.6 mm focal spot size X-ray tube, a 40 cm Thales image intensifier, and a high speed digital camera (Vision Research Phantom v10, 1800×2400 pixels @ 500 frames/s, 14-bit dynamic range). The EMD X-ray generators were customized for us (by the manufacturer) to provide 1 ms pulses at repetition rates up to 180 Hz, for a dose reduction of 4-16× (depending on frame rate) relative to continuous operation.

Position sensing of the subject is performed (block 804) so that automatic gantry repositioning (block 806) can maintain a desired dynamic view of the selected portion of the subject. Alternatively, the subject can be tethered to guide or constrain their movement. The sequence of high speed pulses that construct the biplane X-ray images are closely sequenced so that correlations in time are possible to achieve a 3D dynamic model, but also by minimizing or avoiding Compton scattering interference (block 808). With the collected biplane X-ray imagery, processing can create the desired results of measuring joint position with model-based tracking (block 810) with reference to a previously obtained 3D bone model from a prior CT scan (block 812).

Figure 9:
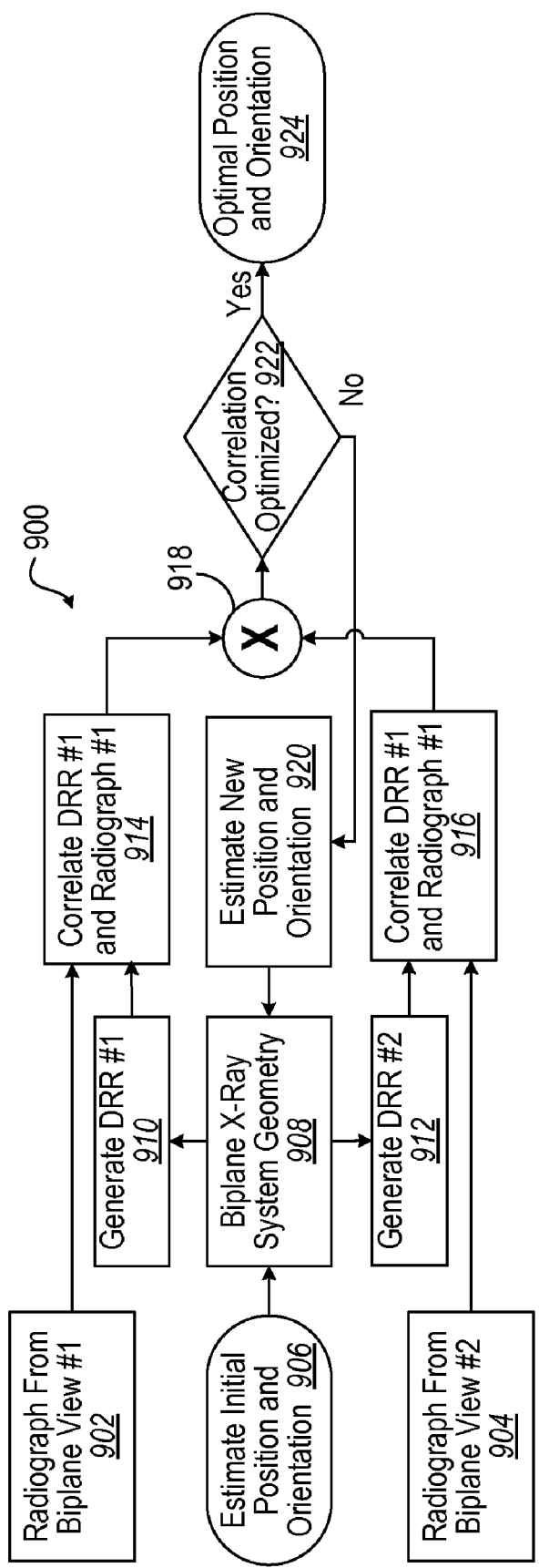
FIG. 9 is a flow diagram for Model-Based Tracking for the methodology of FIG. 8.

In FIG. 9, an illustrative model-based tracking methodology 900 begins by selecting a point in the motion for analysis, such as by visually selecting based upon bone orientation, sensed force on the treadmill, etc. Thereby, an actual radiograph from the first biplane view is selected (block 902) and an actual radiograph from the second biplane view is selected (block 904). Manually or automatically an initial estimate is made of the position orientation of the selected portion of the subject's body as rendered in the 3D bone model (block 906). Knowledge of the biplane X-ray system geometry is accessed (block 908). By orienting the 3D bone model to match an initial estimate of the first biplane radiograph, a first digitally reconstructed radiographs (DRR) can be created (block 910) and a second DRR can be created (block 912). These DRRs can be generated via ray-traced projection through the 3D bone model.

Each DRR is correlated against the respective radiograph biplane view (blocks 914, 916). The error results are combined (block 918) and a new estimate of position and orientation are made (block 920), repeating the correlations in order to optimize the similarity to a desired limit. Once optimization is determined (block 922), then the optimal position and orientation are achieved (block 924) and the results can be used for evaluating the selected portion of the subject's body. In particular, by optimizing the similarity between the two DRRs and the actual 2D biplane radiographic images, the in vivo position and orientation of a given bone can be estimated. Sobel edge-detector output is added to the base images for both the DRRs and the radiographs to enhance the matching process. Match quality is measured by calculating the correlation coefficient of each DRR with its corresponding radiograph, then multiplying the two view correlations to get total system correlation.

The first step in the model-based tracking involved developing the 3D volumetric bone model. First, images of the bone to be tracked were manually segmented from other bones and soft tissue. The CT volume was then interpolated using a feature-based interpolation technique and scaled to have cubic voxels with dimensions similar to the 2D pixel size in the biplane X-ray system images.

The model-based tracking process is performed with an operator-friendly workbench of graphical tools. This workbench includes the following tools: (1) a visual overlay of the DRRs on the radiographs that facilitates the operator's initial guesses and provides contrasting colors to help the operator match position and orientation, (2) an array of six slider bars that control the position and orientation of the model, (3) a low-resolution 2D search tool that performs a wide-latitude, exhaustive search by translating and rotating each DRR to maximize the correlation with its radiograph, (4) a high-resolution (but narrow latitude) six-axis search tool to refine position and orientation, (5) a linear-projection tool that uses the solution from two successive frames to calculate a starting guess for the next frame and then optimizes the solution with the 2D and six-axis search tools, (6) tools for charting the motion and visualizing a movie of successive frames to help the operator evaluate the quality of the automated solution, and (7) an interpolation tool that corrects poor quality solution frames by calculating linear, quadratic, or cubic interpolations based on frames with known good solutions.

Initial estimates for bone position and orientation were obtained by manually adjusting the six motion parameters (three positions, three rotations) to obtain a good visual match between fluoroscopic images and DRRs for both biplane views (FIG. 1). The program measured the quality of the initial guess by generating a DRR for each of the biplane views, enhancing each view by adding a Sobel edge detector output to the original DRR, calculating the correlation coefficient of each DRR with its corresponding radiograph, and multiplying the two correlation coefficients to get a system-correlation measure. The initial guess was improved using the low-resolution 2D search tool that iterated several (typically 2-10) times until the correlation stopped improving. The solution was further refined with the high-resolution six-axis search tool which determined the six-coordinate gradient of the correlation product with finite differences and performed a quadratic search along the gradient line for the maximum correlation product. This process was repeated until the new guess changed by less than 0.1 mm and 0.1 deg for three successive iterations. Initial guesses were made manually for the first two frames in each motion sequence. Since the rapid frame rate minimized differences in joint position between frames, the initial guess for each successive frame was obtained by making a linear projection from the solution of the previous two frames. Thus, the final solution of the previous two frames was used to provide an initial starting point for the subsequent frame. Tracking for the remainder of the motion sequence proceeded without additional user interaction.

In a prototype implementation, the tracking workbench program (not shown) was accelerated by parallelizing its calculations on a cluster of 13 inexpensive microcomputers (e.g., 3.4 GHz Pentium 4, Silicon Mechanics iServ R100, Seattle, Wash.) linked by a gigabit Ethernet switch. This decreased the time required to track a scapula from approximately 8 h on a single personal computer (e.g., 3.4 GHz Pentium 4) to approximately 40 min on the parallel processing system. For a typical trial, each frame of data requires approximately 40-50 s of computing time for the solution to converge. The operator's workstation controls the search processes with a parallel state-machine algorithm, but delegates the computation-intensive DRR projection, edge enhancement, and correlation calculations to the 12 worker nodes. The nodes are scheduled dynamically using standard multiphonon ionization (MPI) protocols. Results are consolidated and presented graphically by the operator's workstation. Using this model-based tracking technique, the 3D position and orientation of the humerus and scapula were determined independently for all frames of each trial. The final step involved determining the position of the tantalum beads within the CT bone model and then expressing their 3D position relative to a fixed laboratory coordinate system. These data enabled a direct comparison between marker-based and model-based tracking results.

Measuring Joint Position with Dynamic RSA. For comparison, the 3D position of each implanted tantalum bead was also determined from the biplane images using an established procedure that was developed and validated in our laboratory. This procedure has been used extensively to measure knee kinematics in humans and canines. The process for moving from digital biplane radiographs to 3D bead coordinates involved image distortion and nonuniformity correction, automated detection of beads from X-ray images, 2D bead centroid calculations, interactive 3D tracking and low-pass filtering. This process determined the 3D location of each tantalum bead relative to the same laboratory coordinate system used by the model-based tracking technique. This RSA approach for measuring the position of implanted tantalum beads has been shown to be accurate to within ±0.1 mm.

Figure 10:
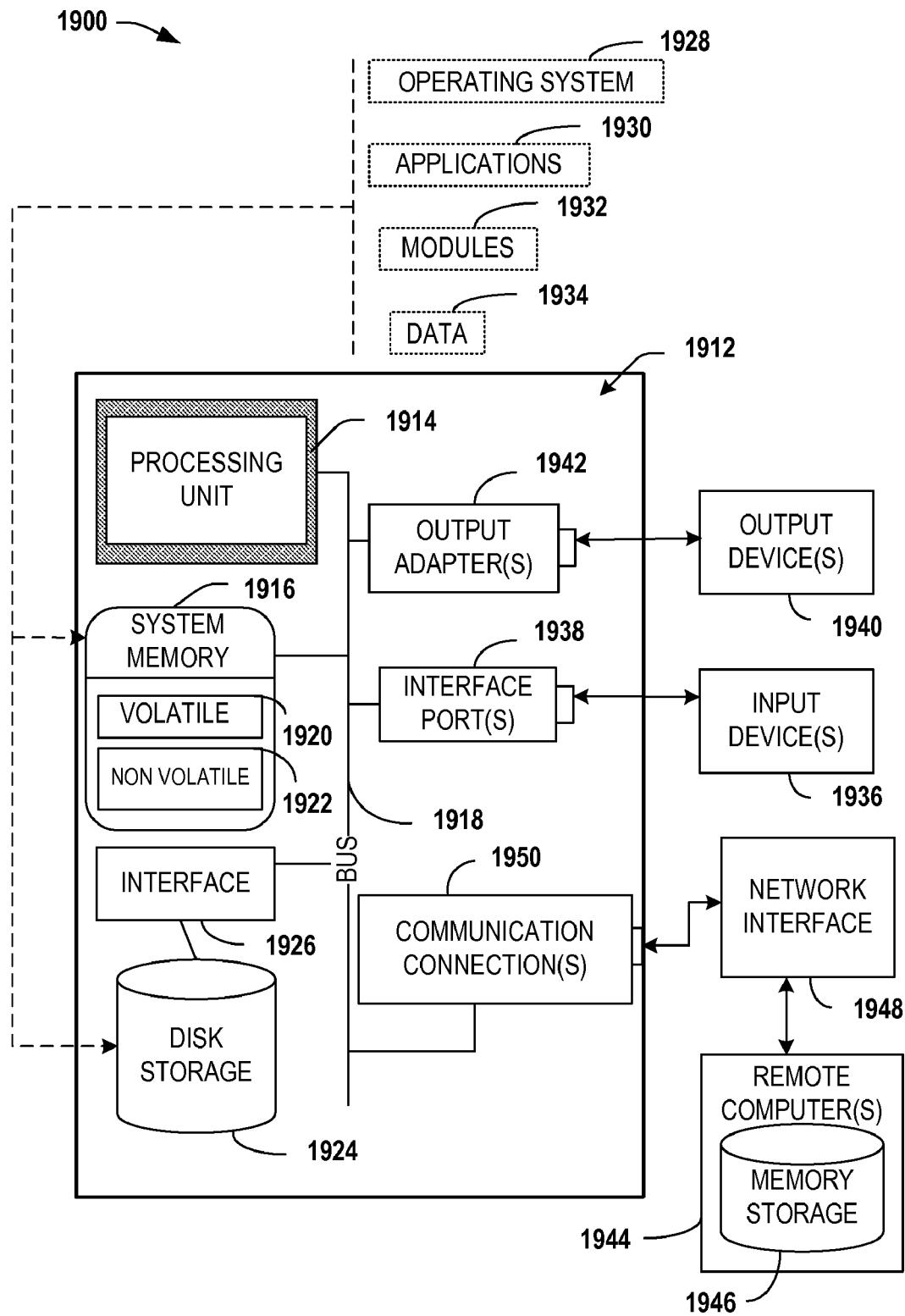
FIG. 10 is a block diagram of an exemplary computing environment for the methodology of FIG. 8.

With reference to FIG. 10, an exemplary environment 1900 for implementing various aspects of the claimed subject matter includes a computer 1912. The computer 1912 includes a processing unit 1914, a system memory 1916, and a system bus 1918. The system bus 1918 couples system components including, but not limited to, the system memory 1916 to the processing unit 1914. The processing unit 1914 can be any of various available processors. Dual microprocessors and other multiprocessor architectures also can be employed as the processing unit 1914.

The system bus 1918 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1916 includes volatile memory 1920 and nonvolatile memory 1922. The basic input/output system (BIOS), containing the basic routines to transfer information between elements within the computer 1912, such as during start-up, is stored in nonvolatile memory 1922. By way of illustration, and not limitation, nonvolatile memory 1922 can include read only memory (ROM), programmable ROM (PROM), electrically programmable ROM (EPROM), electrically erasable programmable ROM (EEPROM), or flash memory. Volatile memory 1920 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM).

Computer 1912 also includes removable/non-removable, volatile/non-volatile computer storage media. FIG. 23 illustrates, for example, disk storage 1924. Disk storage 1924 includes, but is not limited to, devices like a magnetic disk drive, floppy disk drive, tape drive, Jaz drive, Zip drive, LS-100 drive, flash memory card, or memory stick. In addition, disk storage 1924 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1924 to the system bus 1918, a removable or non-removable interface is typically used such as interface 1926.

It is to be appreciated that FIG. 23 describes software that acts as an intermediary between users and the basic computer resources described in the suitable operating environment 1900. Such software includes an operating system 1928. Operating system 1928, which can be stored on disk storage 1924, acts to control and allocate resources of the computer system 1912. System applications 1930 take advantage of the management of resources by operating system 1928 through program modules 1932 and program data 1934 stored either in system memory 1916 or on disk storage 1924. It is to be appreciated that the claimed subject matter can be implemented with various operating systems or combinations of operating systems.

A user enters commands or information into the computer 1912 through input device(s) 1936. Input devices 1936 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1914 through the system bus 1918 via interface port(s) 1938. Interface port(s) 1938 include, for example, a serial port, a parallel port, a game port, and a universal serial bus (USB). Output device(s) 1940 use some of the same type of ports as input device(s) 1936. Thus, for example, a USB port may be used to provide input to computer 1912 and to output information from computer 1912 to an output device 1940. Output adapter 1942 is provided to illustrate that there are some output devices 1940 like monitors, speakers, and printers, among other output devices 1940, which require special adapters. The output adapters 1942 include, by way of illustration and not limitation, video and sound cards that provide a means of connection between the output device 1940 and the system bus 1918. It should be noted that other devices and/or systems of devices provide both input and output capabilities such as remote computer(s) 1944.

Computer 1912 can operate in a networked environment using logical connections to one or more remote computers, such as remote computer(s) 1944. The remote computer(s) 1944 can be a personal computer, a server, a router, a network PC, a workstation, a microprocessor based appliance, a peer device or other common network node and the like, and typically includes many or all of the elements described relative to computer 1912. For purposes of brevity, only a memory storage device 1946 is illustrated with remote computer(s) 1944. Remote computer(s) 1944 is logically connected to computer 1912 through a network interface 1948 and then physically connected via communication connection 1950. Network interface 1948 encompasses wire and/or wireless communication networks such as local-area networks (LAN) and wide-area networks (WAN). LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1950 refers to the hardware/software employed to connect the network interface 1948 to the bus 1918. While communication connection 1950 is shown for illustrative clarity inside computer 1912, it can also be external to computer 1912. The hardware/software necessary for connection to the network interface 1948 includes, for exemplary purposes only, internal and external technologies such as, modems including regular telephone grade modems, cable modems and DSL modems, ISDN adapters, and Ethernet cards.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

For example, an alternative gantry support structure can underlie rather than hanging down about a subject, such as providing a treadmill support that is positioned above a central pivoting hub.

As another example, another alternative gantry support structure can have arms that can be positioned at an angle relative to the vertical.

Moreover, various aspects or features described herein can be implemented as a method, apparatus, or article of manufacture using standard programming or engineering techniques. Further, the operations or actions of a method or algorithm described in connection with the aspects disclosed herein can be embodied directly in hardware, in a software module executed by a processor, or in a combination of the two. Additionally, in some aspects, the operations or actions of a method or algorithm can reside as at least one or any combination or set of codes or instructions on a machine-readable medium or computer readable medium, which can be incorporated into a computer program product. Further, the term "article of manufacture" as used herein is intended to encompass a computer program accessible from any computer-readable device, carrier, or media. For example, computer-readable media can include but are not limited to magnetic storage devices (e.g., hard disk, floppy disk, magnetic strips, etc.), optical disks (e.g., compact disk (CD), digital versatile disk (DVD), etc.), smart cards, and flash memory devices (e.g., card, stick, key drive, etc.). Additionally, various storage media described herein can represent one or more devices or other machine-readable media for storing information. The term "machine-readable medium" can include, without being limited to, wireless channels and various other media capable of storing, containing, or carrying instruction, or data.

In addition to the foregoing, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. Furthermore, as used in this application and the appended claims, the term "or" is intended to mean an inclusive "or" rather than an exclusive "or." That is, unless specified otherwise, or clear from context, "X employs A or B" is intended to mean any of the natural inclusive permutations. That is, in this example, X could employ A, or X could employ B, or X could employ both A and B, and thus the statement "X employs A or B" is satisfied under any of the foregoing instances. In addition, the articles "a" and "an" as used in this application and the appended claims should generally be construed to mean "one or more" unless specified otherwise or clear from context to be directed to a singular form.

As used herein, the terms to "infer" or "inference" refer generally to the process of reasoning about or deducing states of a system, environment, or user from a set of observations as captured via events or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events or data. Such inference results in the construction of new events or actions from a set of observed events or stored event data, whether or not the events are correlated in close temporal proximity, and whether the events and data come from one or several event and data sources.

What is claimed is:

1. An apparatus for dynamic radiographical imaging of skeletal motion of a subject, comprising:
a first overhead support structure comprising a first vertically and horizontally adjustable source arm having a first source arm upper guide configured with a first hollow portion, the source arm positions a first radiological imaging source at a first source position and comprising a first vertically and horizontally adjustable imaging arm having a first imaging arm upper guide configured with a second hollow portion, the imaging arm positions a first radiological imaging receiver at a first imaging position selected for radiological imaging on a first axis passing through a selected portion of the subject;
a second overhead support structure comprising a second vertically and horizontally adjustable source arm that positions a second radiological imaging source at a second source position and comprising a second vertically and horizontally adjustable imaging arm that positions a second radiological imaging receiver at a second imaging position selected for radiological imaging along a second axis intersecting the first axis and passing through the selected portion of the subject, wherein opposing ends of the second overhead support structure slideably enter the first hollow portion or the second hollow portion to facilitate orientation of the first axis and the second axis;
position references coupled between the first and second support structures that determine relative orientation between the first and second axes; and
an imaging system that generates three-dimensional radiology image data that dynamically changes as the subject moves by processing bi-planar radiological imaging data received from the first and second imaging receivers.

2. The apparatus of claim 1, further comprising a gantry pivoting hub assembly that rotates the first overhead support structure relative to the second overhead support structure for selecting an orientation between the first and second axes of up to and including 90°, wherein rotation of the first overhead support structure pivots the first radiological imaging source and the first radiological imaging receiver in synchronization relative to each other, and wherein rotation of the second overhead support structure pivots the second radiological imaging source and the second radiological imaging receiver in synchronization relative to each other.

3. The apparatus of claim 2, the first overhead support structure and the second overhead support structure facilitate translation of the gantry pivoting hub assembly in one horizontal direction.

4. The apparatus of claim 3, the first overhead support structure and the second overhead support structure facilitate translation of the gantry pivoting hub assembly in a horizontal plane.

5. The apparatus of claim 2, wherein the first and second overhead support structures each comprise a beam attached to pivot horizontally about the gantry pivoting hub assembly, the second overhead support structure below the first overhead support structure.

6. The apparatus of claim 5, wherein the gantry pivoting hub assembly comprises a first attachment that facilitates translation of the first beam of the first overhead support structure and comprises a second attachment that facilitates translation of the second beam of the second overhead support structure.

7. The apparatus of claim 5, wherein the first and second overhead support structure each comprise a downwardly telescoping originating arm terminating in a pivoting attachment to the respective radiological imaging source and comprise a downwardly telescoping receiving arm terminating in a pivoting attachment to the respective radiological imaging receiver.

8. The apparatus of claim 1, further comprising a treadmill positioned below the first and second axes for supporting the subject, wherein the skeletal motion of the selected portion of the subject comprises at least one of a knee, shoulder, spine, hip, ankle or foot region.

9. The apparatus of claim 1, further comprising a subject position sensor for determining position of the selected portion relative to the first and second axes.

10. The apparatus of claim 1, further comprising a plurality of actuators for powered positioning of the first and second overhead support structures.

11. The apparatus of claim 10, further comprising:
a subject position sensor for determining position of the selected portion relative to the first and second axes; and
an automatic positioning system for controlling a plurality of actuators to maintain the first and second axes in a desired position relative to the subject as the subject moves.

12. The apparatus of claim 1, further comprising a pulse sequencing component for deconflicting pulses emitted by the first and second radiological imaging sources to avoid Compton scattering interference received by the other respective radiological imaging receiver, wherein a pulse from the second radiological source is triggered immediately following a pulse triggered from the first radiological source, wherein pulse and delay between each pulse is independent of frame rate.

13. The apparatus of claim 1, wherein the first and second radiological imaging receivers comprise flat panel imagers.

14. The apparatus of claim 1, wherein the imaging system generates dynamically changing three-dimensional radiology imaging data by,
triggering a first pulse from a first imaging source and second pulse from a second imaging source, wherein the first pulse and second pulse are delayed independent of frame rate and wherein the frame rate is between 5 and 180 frames per second;
obtaining a pair of two-dimensional biplane radiographic images from the respective first and second radiological imaging receivers;
generating a pair of digitally reconstructed radiographs (DRRs) by ray-tracing projection through a three-dimensional model previously obtained by three-dimensional imaging of the selected portion of the subject; and
optimizing similarity between the two DRRs and the two-dimensional biplane radiographic images to estimate in vivo position and orientation of an imaged skeletal structure within the selected portion of the subject.

15. An apparatus for supporting two biplane radiographic imaging systems used to obtain dynamic three dimensional radiological images, comprising:
a gantry pivoting hub assembly having a disc brake assembly, an upper sleeve supporting a first beam and a lower sleeve housing supporting a second beam, the first and second sleeves attached for horizontal rotation relative to each other and a support surface, wherein the disc brake assembly controls rotation speed of the upper and lower beams;
a first telescoping originating arm attached to an upper guide that translates on one end of the first beam and terminating in a vertically pivoting attachment for a first radiological source;
a first telescoping receiving arm attached to an upper guide that translates on another end of the first beam and terminating in a vertically pivoting attachment for a first radiological receiver, wherein each of the upper guides include a hollow portion configured to accept a portion of the second beam;
a second telescoping originating arm attached to translate on one end of the second beam and terminating in a vertically pivoting attachment for a second radiological source; and
a second telescoping receiving arm attached to translate on another end of the second beam and terminating in a vertically pivoting attachment for a second radiological receiver, the second beam shorter than the first beam to allow alignment of the first and second beams with the first telescoping originating and receiving arms positionable to avoid contacting the second beam.

16. The apparatus of claim 15, further comprising motorized actuators for closed loop positioning of each pivoting, translating, and telescoping component.

17. The apparatus of claim 15, further comprising:
a first pair of parallel horizontal rails; and
a second pair of parallel horizontal rails horizontally orthogonal to and attached for translation along the first pair of parallel horizontal rails, the gantry pivoting hub assembly attached for translation along the second pair of parallel horizontal rails.

18. The apparatus of claim 17, further comprising motorized actuators for closed loop positioning of translating the gantry pivoting hub assembly along the second pair of parallel horizontal rails and for translating the second pair of parallel horizontal rails relative to the first pair of horizontal rails.

19. A method, comprising:
adjusting connected supporting structures that independently position biplane radiological imaging components whose adjustable imaging axes intersect through a selected portion of a subject;
determining a relative orientation between the adjustable imaging axes based upon the adjustable connected supporting structures,
wherein the adjustable imaging axes are vertically adjustable down to 0 degrees relatively and horizontally adjustable down to 0 degrees;
obtaining a pair of two-dimensional biplane radiographic images from the biplane radiological imaging components, wherein the pair of two-dimensional biplane radiographic images are captured via 1 ms pulses that are triggered slightly more than 1 ms from each other; and
generating that dynamically chap es as the subject moves by processing the pair of two-dimensional biplane radiological images.

20. The method of claim 19, further comprising:
dynamically positioning each of the connected supporting structures via positioning actuator controls that provide absolute positioning information within a room.

* * * * *